US006546352B2

(12) United States Patent
Jahn

(10) Patent No.: US 6,546,352 B2
(45) Date of Patent: Apr. 8, 2003

(54) METHOD AND APPARATUS FOR EVALUATION OF AGGREGATE PARTICLE SHAPES THROUGH MULTIPLE RATIO ANALYSIS

(75) Inventor: David Jahn, Cincinnati, OH (US)

(73) Assignee: Martin Marietta Materials, Inc., Raleigh, NC (US)

( * ) Notice: Subject to any disclaimer, the term of this patent is extended or adjusted under 35 U.S.C. 154(b) by 0 days.

(21) Appl. No.: 09/832,182

(22) Filed: Apr. 11, 2001

(65) Prior Publication Data

US 2002/0042689 A1 Apr. 11, 2002

Related U.S. Application Data

(60) Provisional application No. 60/196,161, filed on Apr. 11, 2000.

(51) Int. Cl.[7] .................. G06M 11/04; G01N 15/00
(52) U.S. Cl. .................. 702/128; 73/865.5; 366/8; 324/71.4
(58) Field of Search .................. 702/26, 35, 128, 702/155, 179; 73/38, 104, 861.41, 865.5; 241/24.1; 324/71.4; 377/11; 366/8; 700/97

(56) References Cited

U.S. PATENT DOCUMENTS

| 3,678,759 A | * | 7/1972 | Schneeberger | 73/865.5 |
|---|---|---|---|---|
| 3,719,089 A | * | 3/1973 | Kelsall et al. | 73/865.5 |
| 3,739,180 A | * | 6/1973 | Carlson | 377/11 |
| 3,869,110 A | * | 3/1975 | Brock et al. | 366/8 |
| 4,627,576 A | * | 12/1986 | Hahn et al. | 241/24.1 |
| 4,935,616 A | | 6/1990 | Scott | 250/214 VT |
| 5,049,540 A | | 9/1991 | Park et al. | 505/400 |
| 5,376,878 A | * | 12/1994 | Fisher | 324/71.4 |
| 5,576,449 A | * | 11/1996 | Davies | 73/861.41 |
| 5,578,771 A | * | 11/1996 | Karhu | 73/865.5 |
| 5,721,433 A | | 2/1998 | Kosaka | 250/573 |
| 5,943,234 A | * | 8/1999 | Martinez | 700/97 |
| 6,145,390 A | * | 11/2000 | Jahn et al. | 73/865.5 |
| 6,230,552 B1 | * | 5/2001 | Able et al. | 73/104 |
| 6,269,681 B1 | * | 8/2001 | Hara et al. | 73/38 |
| 6,294,685 B1 | | 9/2001 | Ushikubo et al. | 558/319 |
| 6,454,862 B1 | | 9/2002 | Yoshida et al. | 118/722 |

OTHER PUBLICATIONS

PCT International Search Report dated Jul. 26, 2001.
"Along the road", Public Roads; Washington; Mar./Apr. 1999; Anonymous, vol. 62, Issue 5, Copyright Superintendent of Documents.

* cited by examiner

Primary Examiner—John Barlow
Assistant Examiner—John Le
(74) Attorney, Agent, or Firm—McDermott, Will & Emery

(57) ABSTRACT

A method and apparatus for performing multiple ratio analysis of aggregate particles, wherein the method includes the steps of measuring a first maximum dimension of a particle, measuring a second maximum dimension of a particle in a direction substantially perpendicular to the first maximum dimension, and inputting the first maximum dimension and second maximum dimension into a computer having a processor. Using the computer, a particle ratio of the first maximum dimension to the second maximum dimension for the measured particle is computed and the particle ratio is classified into one of a predetermined plurality of different ratio ranges, each of these plurality of different ratios representative of a different range of particle shapes. An apparatus for multiple ratio analysis includes a measurement device configured to measure a dimension of an aggregate particle along at least one axis at a time, a computer, and a program or instruction set permitting calculation of an aggregate particle ratio for the aggregate particle and classifying this aggregate particle ratio, as noted.

23 Claims, 13 Drawing Sheets

Multiple Ratio Analysis (weighted average) of a limestone

MRA of fractional sizes present in Fig. 1

| Max | 22.51 | | | | | |
|-----|-------|-----|------|-----|-----|-----|
| Min | 4.28  | 5.3 | 5.26 | 5.3 | 5.3 | 5.3 |
| Max | 23.71 | | | | | |
| Min | 5.35  | 4.4 | 4.43 | 4.4 | 4.4 | 4.4 |
| Max | 11.15 | | | | | |
| Min | 6.78  | 1.6 | 1.64 | 1.6 | 1.6 | 1.6 |
| Max | 15.21 | | | | | |
| Min | 4.06  | 3.7 | 3.75 | 3.7 | 3.7 | 3.7 |
| Max | 15.72 | | | | | |
| Min | 4.50  | 3.5 | 3.49 | 3.5 | 3.5 | 3.5 |
| Max | 20.23 | | | | | |
| Min | 7.06  | 2.9 | 2.87 | 2.9 | 2.9 | 2.9 |

Portion of a spreadsheet showing automated color coding for MRA ratios

MRA on the same sample by two different operators

MRA Data Information Area
Enter g Weights After Analyzing Particles

| Sieve Fractions | 2:1 | 3:1 | 4:1 | 5:1 | Total Mass By Fraction |
|---|---|---|---|---|---|
| 2 x 1 1/2 | | | | | |
| Percent of Fraction | | | | | |
| 1 1/2 x 1 | 1284.3 | 2270.7 | 1593.5 | 552.3 | 600.3 | 6,301.1 |
| Percent of Fraction | 20.4% | 36.0% | 25.3% | 8.8% | 9.5% | |
| 1 x 3/4 | 302.9 | 833.0 | 865.4 | 346.3 | 181.3 | 2,528.9 |
| Percent of Fraction | 12.0% | 32.9% | 34.2% | 13.7% | 7.2% | |
| 3/4 x 1/2 | 211.6 | 642.6 | 433.3 | 288.5 | 397.4 | 1,973.4 |
| Percent of Fraction | 10.7% | 32.6% | 22.0% | 14.6% | 20.1% | |
| 1/2 x 3/8 | 77.0 | 150.4 | 181.1 | 105.5 | 174.4 | 688.4 |
| Percent of Fraction | 11.2% | 21.8% | 26.3% | 15.3% | 26.3% | |
| 3/8 x #4 | 11.6 | 24.5 | 29.3 | 24.9 | 40.1 | 130.4 |
| Percent of Fraction | 8.9% | 18.8% | 22.5% | 19.1% | 30.8% | |
| Total g | | | | | | 11,622.2 |

MRA calculation portion of a spreadsheet

FIG. 10

MRA of minus 1 1/2 inch basalt fractions after secondary crushing

MRA of minus 3/4 inch basalt particles after tertiary crushing

METHOD AND APPARATUS FOR EVALUATION OF AGGREGATE PARTICLE SHAPES THROUGH MULTIPLE RATIO ANALYSIS

CROSS REFERENCE TO RELATED APPLICATIONS

This application claims priority to the filing date of Provisional Application Ser. No. 60/196,161, filed Apr. 11, 2000, the disclosure of which is hereby incorporated by reference.

BACKGROUND OF THE INVENTION

Aggregates, including for example crushed stone, sand and gravel, are one of the most fundamental components used in construction.

Approximately fifty percent of aggregates are shipped for highway construction, either as road base or a primary component of asphalt and concrete. Aggregates are also used in commercial and residential construction as base for foundations, concrete and parking lots. Other uses for aggregates, some of which require a high-quality, chemical-grade limestone, include: riprap for erosion control; railroad ballast; flux stone; filter stone; agricultural limestone; production of cement and lime; desulfurization; acid neutralization; animal feed supplements; and plastic and paint fillers. Regardless of the use, the production requirements of stone aggregates are complex because the material must be crushed to multiple sizes, often washed to remove fines and impurities, and sometimes processed further in order to meet the specification for its intended use. Without the physical and chemical properties provided by aggregates, modem construction materials and methods, as well as a multitude of industrial products, would not be possible.

Product requirements often dictate the percentages of flat particles, elongated particles or flat and elongated particles in coarse aggregates. For example, flat or elongated particles of aggregates for some construction uses may interfere with consolidation and result in harsh, difficult to place materials. Flat particles are defined as those particles that exceed a specified ratio of width to thickness. For example, if the ratio is 3:1, the width cannot exceed three times the thickness. (A specification will give a percentage and then the ratio, such as 20% 3:1, meaning a sample fails the specification if more than 20% of the particles (individual pieces or by mass of the total sample) tested have ratios that exceed 3:1.) Elongated particles are defined as those particles that exceed a specified ratio of length to width. Flat or elongated particles are defined as those particles of aggregate having a ratio of width to thickness or length to width greater than a specified value. Flat and elongated particles of aggregate are defined to be those particles having a ratio of length to thickness (maximum to minimum) greater than a specified value.

Sieve size is the size of an opening that a particle can pass through. The specification may require that the amount of particles passing through the opening be determined ("percent passing"). Alternatively, the specification may require that the percent of the sample that does not pass through a specified opening be determined ("percent retained").

Crushers are conventionally used to crush large aggregate particles (e.g., rocks) into smaller particles. One particular type of crusher is known as a cone crusher. A typical cone crusher includes a frame supporting a crusher head and a mantle secured to the head. A bowl and bowl liner are supported by the frame so that an annular space is formed between the bowl liner and the mantle. In operation, large particles are fed into the annular space between the bowl liner and the mantle. The head, and the mantle mounted on the head, rotate eccentrically about an axis, causing the annular space to vary. As the distance between the mantle and the bowl liner varies, the large particles are impacted and compressed between the mantle and the bowl liner. The particles are crushed and reduced to the desired product size, and then drop down from between the mantle and bowl liner.

Aggregate is a description of the product based on how much of the product passes (or could be given as how much is "retained on") a specified number of sieve sizes, or openings. For example, an ASTM (American Society of Testing and Materials) #57, a typical product used in concrete and asphalt construction, is described by using sieve sizes as follows (sieve sizes are square openings):

| Sieve Size | % Passing | |
|---|---|---|
| 1 ½ inches | 100% | 100% of the sample must pass through an 1 ½ inch square opening |
| 1 inch | 95–100% | Between 95 and 100% of the particles must be smaller than 1 inch |
| ½ | 25–60% | Between 25 and 60% of the particles must be smaller than ½ inch |
| #4 | 0–10% | #4 is close to ¼ inch opening |
| #8 | 0–5% | #8 is close to ⅛ inch opening |

Prior apparatus and methods for measuring individual particles of aggregate of specific sieve size to determine the ratio of width to thickness, length to width, or length to thickness include that disclosed in *Standard Test Method for Flat Particles, Elongated Particles or Flat and Elongated Particles, in Coarse Aggregate*, ASTM Designation D 4791-95, the entire contents of which is incorporated herein by reference. This test method uses a proportional caliper device that consists of a base plate with two fixed posts and a swinging arm mounted between them so that the openings between the swinging arm and the two fixed posts maintain a constant ratio. The axis position can be adjusted to provide the desired ratio of opening dimensions. The axis position must be moved to change the ratio being measured. A complete re-measuring of the particle under test each time a new ratio is selected is thus required. This device is therefore capable of measuring only one ratio at a time and is therefore capable of only determining whether a particle is larger or smaller than a single ratio.

Additionally, ASTM D 4791 details how to measure flat and elongated particles using a proportional caliper device that determines pass/fail for one ratio at a time. Specifications are based around using the proportional caliper device and specify the ratio and the maximum percent of the sample that can exceed the given ratio. In the "Superpave" asphalt pavement mix design specification, for example, 10% on a 5:1 ratio means that no more than 10% of the aggregate sample can have a maximum dimension greater than five times the minimum dimension. Most aggregate specifications currently (and historically) use 10% on a 5:1 ratio, which is adequate for controlling excessive flat and elongated particles.

However, describing the flat and elongated particles present in a sample using the percent found at one ratio doesn't give a true picture of the various ratios found within a sample as described later in this paper. A good analogy would be to describe the gradation of an ASTM #57 stone by giving only the percent passing the ½-inch sieve. Without the information on the 1 inch, ¾ inch, ⅜ inch and #4 sieve, a complete picture of the gradation of the sample cannot be determined.

Without a complete picture of the various particle shapes in a sample, it is difficult to accurately evaluate performance results as determined by the current research efforts concerning particle shape. Several Departments of Transportation (DOT's) and universities are developing automated procedures that determine aggregate particle shapes (Button, 2000), however the equipment costs involved (up to $30,000) make these devices far too expensive to be used in the typical aggregate laboratory. In addition, measurements with the automated devices are still aimed at determining the percent found at one specified ratio rather than gathering Multiple Ratio Analysis data.

Accordingly, there is still a need for an inexpensive and readily usable arrangement for determining aggregate particle shapes.

SUMMARY OF THE INVENTION

The present invention is directed to a method and apparatus for compiling data permitting evaluation of aggregate particle shapes.

In one aspect, the invention includes a method for performing multiple ratio analysis of aggregate particles. This method includes the steps of measuring a first maximum dimension of a particle, measuring a second maximum dimension of a particle in a direction substantially perpendicular to the first maximum dimension, and inputting the first maximum dimension and second maximum dimension into a computer having a processor. Using the computer, a particle ratio of the first maximum dimension to the second maximum dimension for the measured particle is computed and the particle ratio is classified into one of a predetermined plurality of different ratio ranges, each of these plurality of different ratios representative of a different range of particle shapes.

Another aspect of the invention includes an apparatus for multiple ratio analysis. This apparatus includes a measurement device configured to measure a dimension of an aggregate particle along at least one axis at a time, a computer, and a computer-readable medium bearing an instruction set executable by the computer. The instruction set permits the computer to calculate an aggregate particle ratio for an aggregate particle by determining a ratio of a first maximum dimension and a second maximum dimension of the aggregate particle. The instruction set also permits the computer to classify the aggregate particle ratio into one of a predetermined plurality of different aggregate particle ratio ranges, each of the plurality of different aggregate particle ratios representative of a different range of aggregate particle shapes.

Still other objects and advantages of the present invention will become readily apparent from the following detailed description, simply by way of illustration of the best modes contemplated of carrying out the invention. As will be realized, the invention is capable of other and different embodiments and its several details are capable of modifications in various obvious respects, all without departing from the invention. Accordingly, the drawings and description are to be regarded as illustrative in nature, and not as restrictive.

BRIEF DESCRIPTION OF THE DRAWINGS

The various features and advantages of the present invention will become more clearly appreciated as a detailed description of a preferred embodiment of the present invention is given with reference to the appended drawings in which:

FIG. 10 shows another spreadsheet image which depicts the MRA calculation;

DETAILED DESCRIPTION OF THE INVENTION

In view of the above, asphalt pavement design, for example, has focused attention on aggregate particle shape requirements. As disclosed herein, a technique referred to as Multiple Ratio Analysis (MRA) has been developed as a method of categorizing the various particle shapes found in an aggregate sample. Improved definition of the various particle shapes found within the coarse aggregate particles leads to improved mix design procedures for performance optimized combined gradations based on particle shape. MRA analysis also lends itself to optimization of crusher performance and measurement of product consistency during production.

Figure 6:
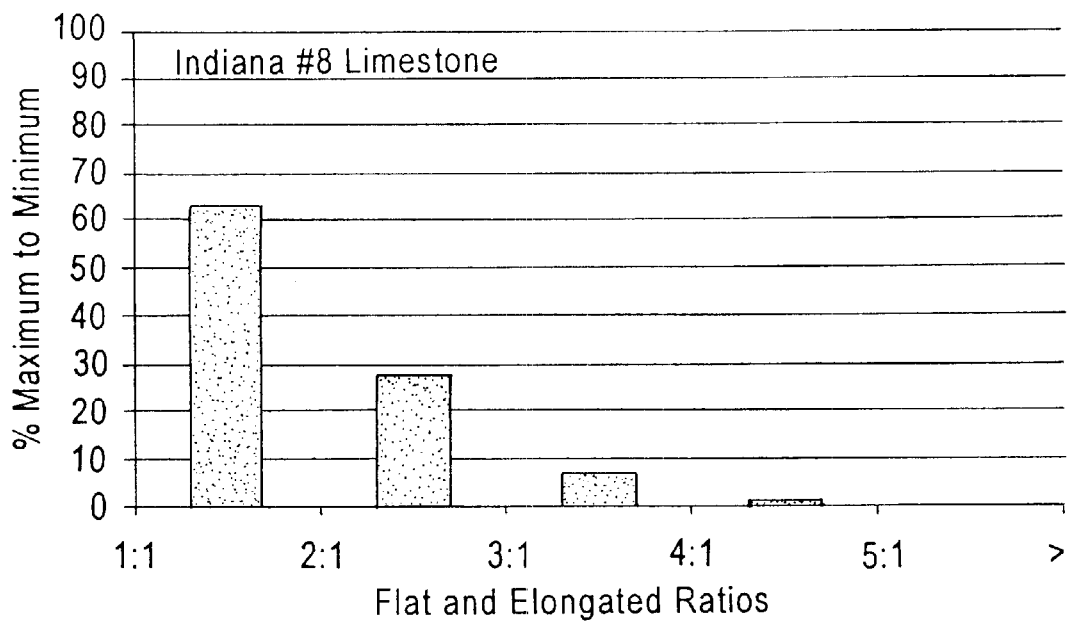
FIG. 6 is a bar graphs which demonstrates a multiple ratio analysis of a limestone in weighted average terms.
Figure 7:
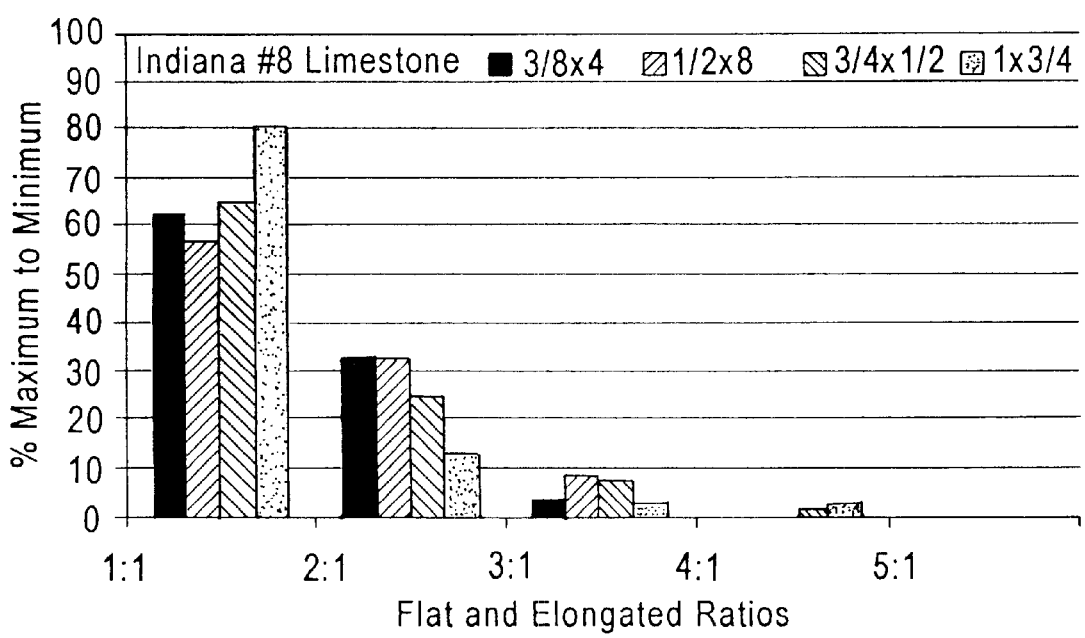
FIG. 7 is a multiple ratio analysis of fractional sizes depicted in FIG. 1.

This MRA technique involves the use of a digital measuring device that easily and more accurately determines the various coarse aggregate particle shapes found in an aggregate sample. More specifically MRA gives an accurate picture of an aggregate sample's particle shapes by evaluating the sample on a plurality of different ratios, such as but not limited to five or more (i.e., <2:1, 2:1 to 3:1, 3:1 to 4:1, 4:1 to 5:1, >5:1), as shown in FIG. 6. Even more information can be gained by examining the MRA of the various size fractions found in the same aggregate sample (FIG. 7).

FIGS. 1–5 show an apparatus which may be used to perform MRA in one embodiment of the present invention. As shown in FIGS. 1–5, this apparatus includes a measurement device or measurement system 100, such as digital caliper (hereinafter digital caliper 100 or measurement device 100), a notebook computer 200 and a foot operated switch 300. The digital caliper 100 is provided with a read-out 102 which is associated with a measuring device which determines the distance between the upper and lower jaws 104 and 106 of the caliper arrangement. A manually operable handle/knob 108 is provided to control the raising and lowering of the upper jaw 104 until it is in contact with a particle which is under examination.

Using the measurement device 100, it is desired to obtain a first measurement along a first maximum dimension of a particle in a manner known to those skilled in the art, as provided in ASTM D4791-99, for example, the entire contents of which are incorporated herein by reference. The first maximum dimension of the particle is the longest dimension of the particle in any direction and is generally defined as the length of the particle. In other words, in a conventional cartesian coordinate system, the first maximum dimension or length could be arbitrarily assigned to correspond to the X-axis.

The width is, accordingly, a plane perpendicular to the length (e.g., Y-axis) and the thickness is a plane perpendicular to both the length and the width (e.g., Z-axis). ASTM D4791-99 defines width as the maximum dimension perpendicular to the length and defines thickness as the maximum dimension perpendicular to both the length and the width. As used hereinafter, the term first maximum dimension shall refer to the particle length and the term second maximum dimension shall refer to the lesser of the width or thickness maximum dimensions. Following the first measurement, a second measurement is taken along this second maximum dimension of the particle in accord with the invention. For the vast majority of particles, it is relatively easy to visually determine length, width, and thickness. For the very few particles where width and thickness appear to be the same, an extra measurement may be taken to confirm that the lesser of the maximum of the thickness and width is selected in accord with the invention. However, appropriate tolerances are designed into the selected ratio ranges, whether two, three, five, or ten ratios are represented, so that essentially the same ratio will be calculated for either the width maximum or the thickness maximum and the particle will be assigned to the same ratio grouping regardless of the dimension selected from the two essentially equal width and thickness in the second maximum measurement. Thus, only two measurements are necessary in accord with the present invention, although additional measurement may certainly be taken to provide additional data integrity or for additional data analysis in accord with the invention. For example, the width maximum could also be measured as a third maximum dimension and calculations may be made comparing length to width (ratio A) and width to thickness (ratio B).

Although arbitrarily designated as first and second measurement, it is to be understood that the measurements could be taken in any order. Further, although it is preferred to obtain the absolute maximum first dimension along the length, width, and thickness, the measurements of the above-noted dimensions are not required to be absolute maximum dimensions. Instead, it is sufficient that the measurements taken are within about 10 to 20% of the relevant length, width, or thickness maximum dimension, as significant useful data in accord with the invention may be obtained therefrom. It is preferred that measurements taken are within at least 5% of the relevant length, width, or thickness maximum dimension.

Figure 1:
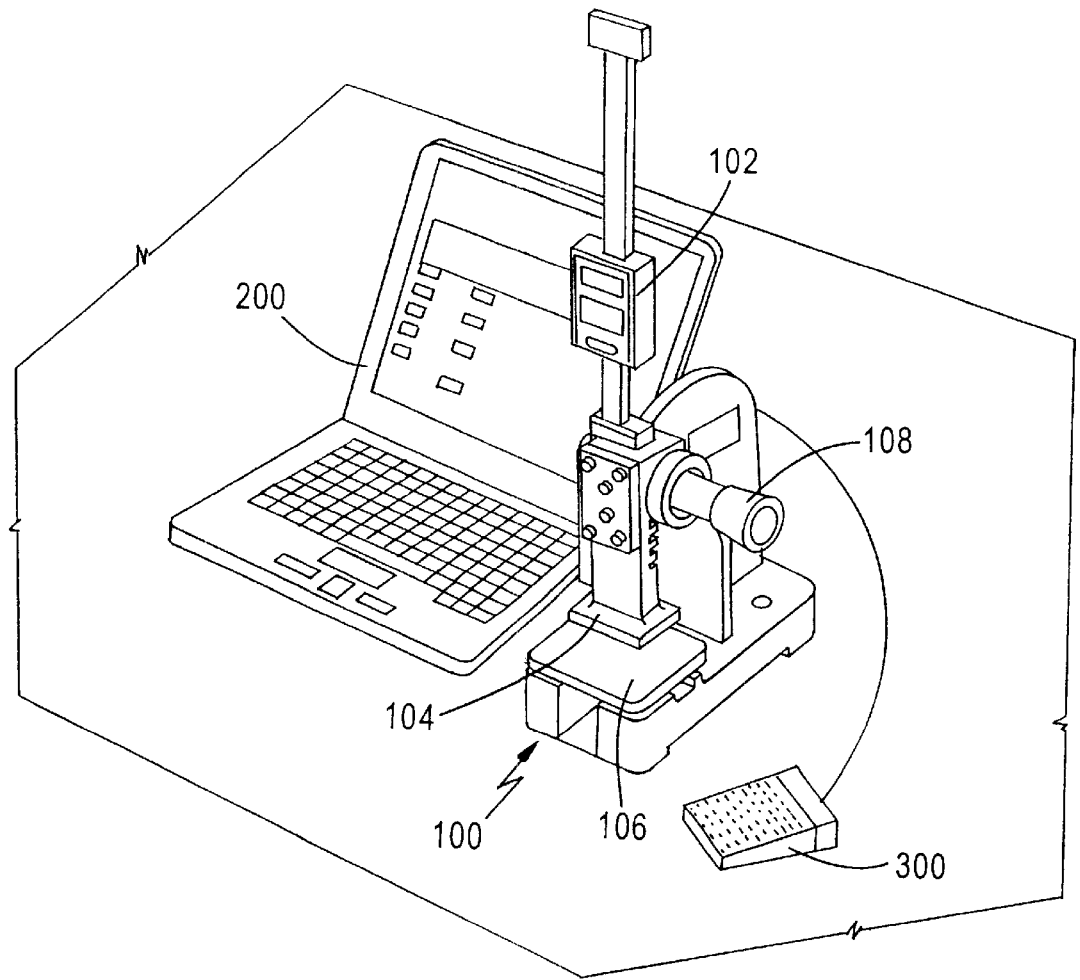
FIG. 1 is a perspective view showing a digital caliper, a laptop personal computer and a manually operated foot switch which are operatively connected/interfaced to enable data to be intermittently uploaded and captured by suitable software loaded in the computer.
Figure 2:
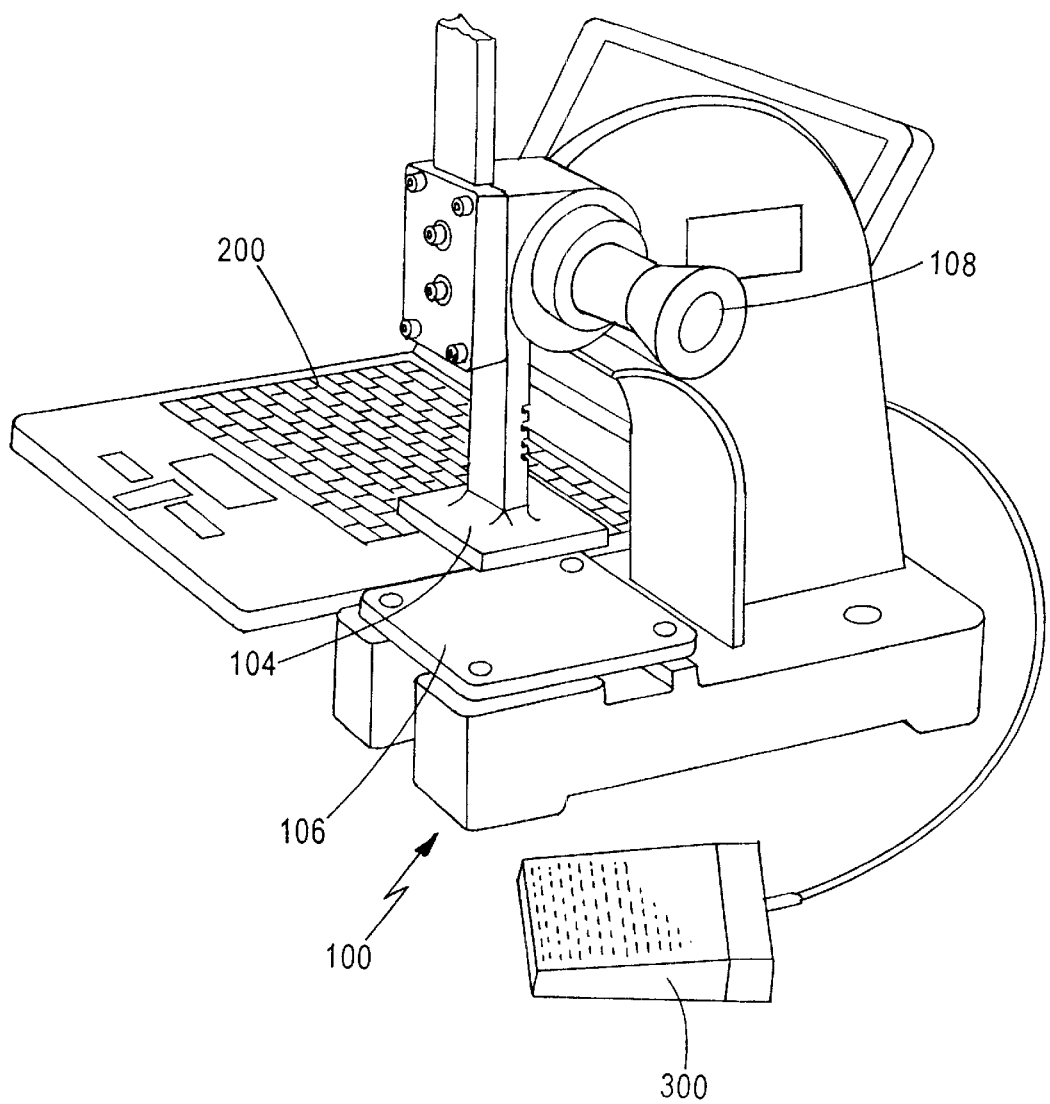
FIG. 2 is a perspective view showing an enlarged view of the digital caliper depicted in FIG. 1.
Figure 3:
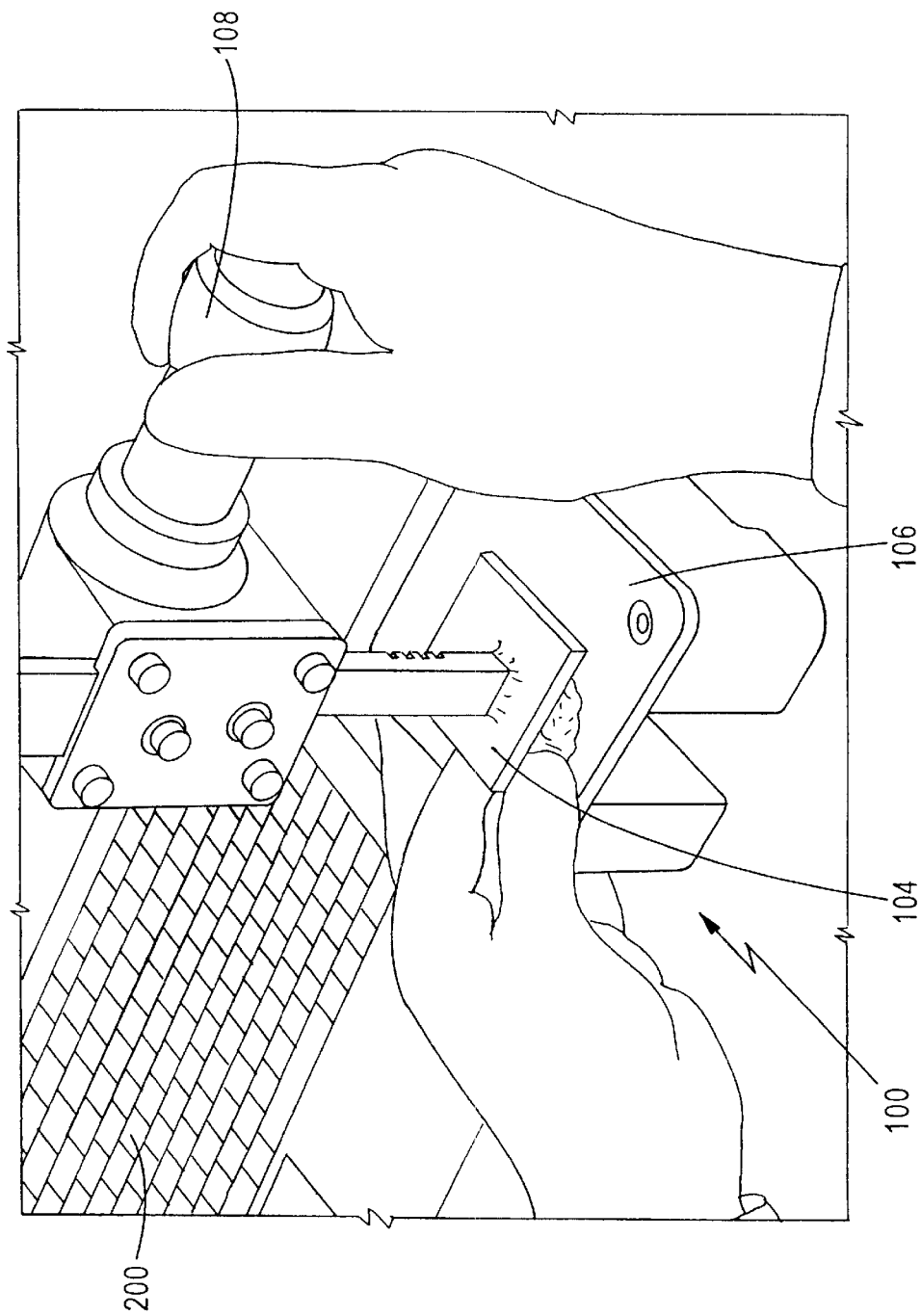
FIG. 3 is a perspective view showing an operator holding a particle in position between the jaws of the caliper and operating the caliper to lower the upper jaw into measuring contact with the particle under examination.
Figure 4:
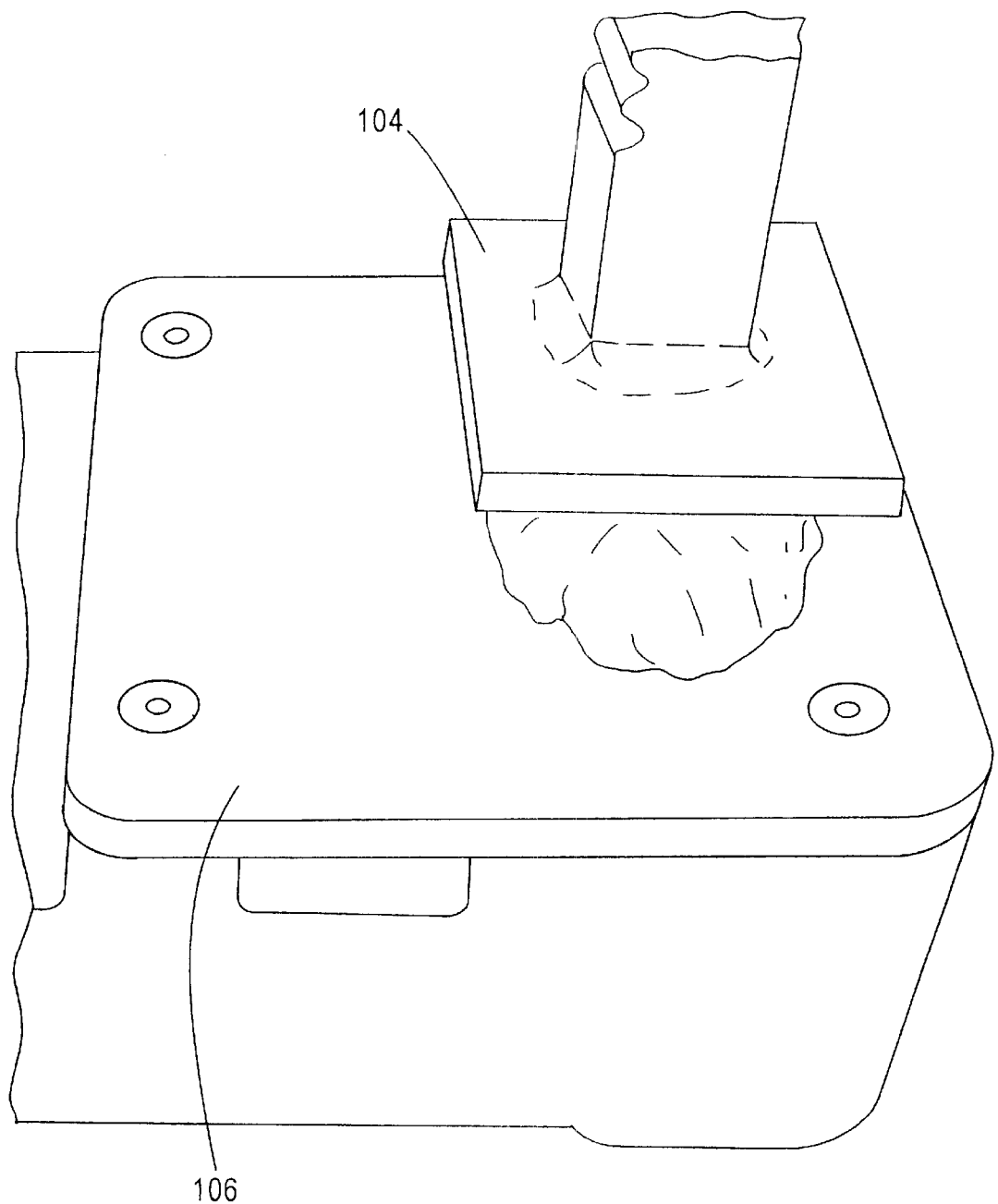
FIGS. 4 and 5 are perspective views showing two different dimensions of a particle being measured between the jaws of the digital caliper.
Figure 5:
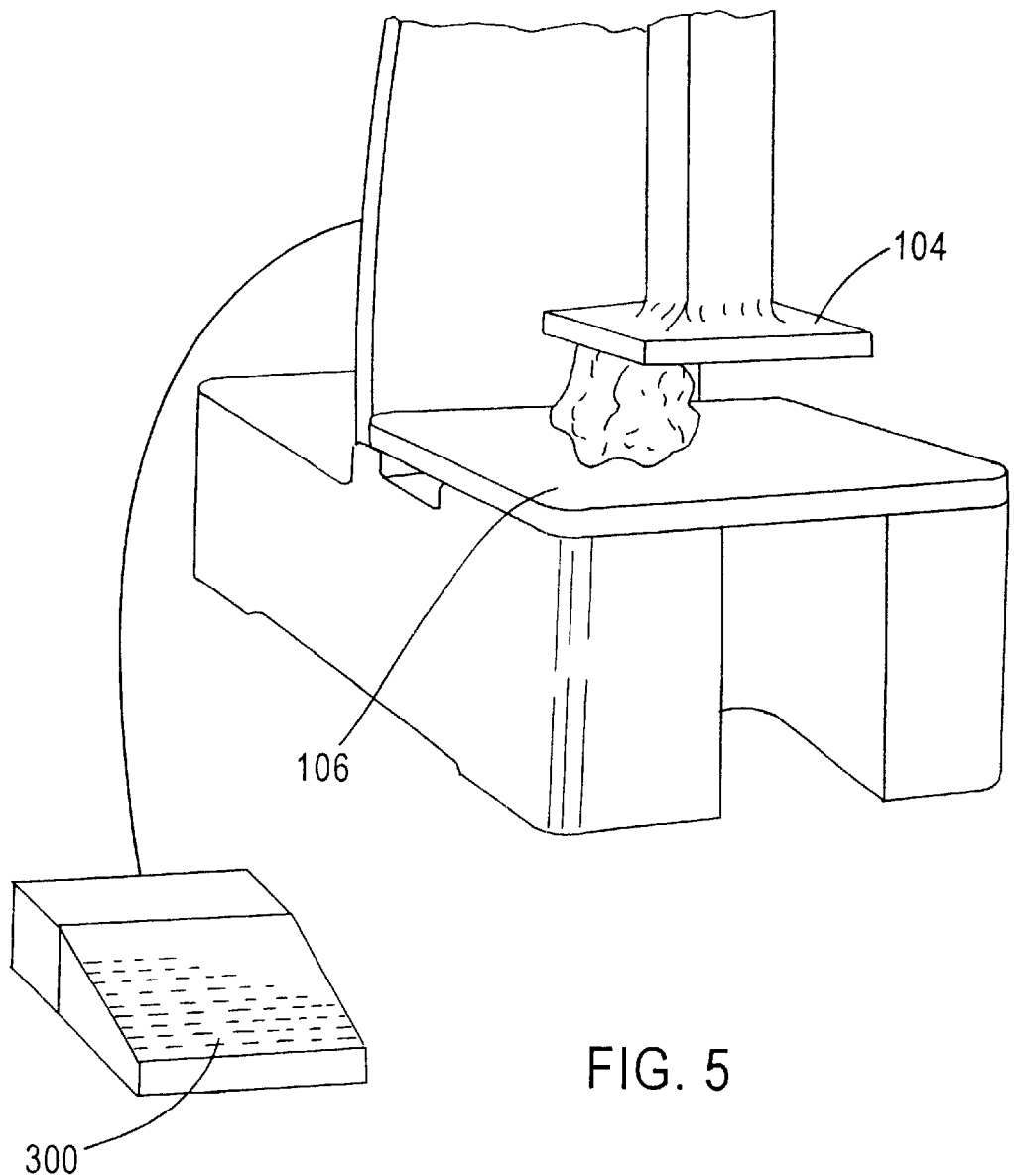

Measurements can be made very rapidly with the above-described digital caliper measuring device 100, notebook computer 200 and foot operated switch 300 combination, which is the preferred embodiment of the invention. As shown in FIGS. 3–5, a technician or operator of the device places the aggregate particle in a desired configuration in the device using the left hand, while using the right hand to rotate the shaft to make the upper platen descend to contact the aggregate particle. A first measurement is taken along the first maximum dimension by pressing the foot operated switch 300. Following raising of the upper platen to release the aggregate particle, the aggregate particle may be repositioned to take a second measurement along the second maximum dimension, in accord with the invention. Using the above sequence of steps and equipment, the MRA ratios may generally be obtained within about two seconds.

Alternatively, measurements may be input into the computer 200 using a keyboard, voice data entry device, mouse, switch, touch sensitive display or data bearing carrier wave, such as but not limited to infrared waves. Further, the above example serves as one possible means to implement the measurement scheme of the invention and is capable of alteration in many forms to best suit the needs of the device operator, the particular model of digital caliper utilized.

In a preferred embodiment, once all of the aggregate particles have been measured and separated into the plurality of ratios, such as by placing the aggregate particles in bins or piles in accord with the designated ratio range, five in the preferred embodiment, the operator weighs the combined aggregate particles for each one of the plurality of ratios and inputs the weight of the combined aggregate particles in the spreadsheet such as by a keyboard, voice data entry device, mouse, switch, touch sensitive display or carrier wave. Thus, the weight of each particle is generally not taken individually, which provides a simple, efficient way to compare total masses of one ratio group to total masses of another ratio group and permits determination of the proportion of the sample in each group by mass in accord with ASTM D 4791-99, § 8.4.3. The computer 200 may then calculate, for example, a weighted average for the total sample, as shown in FIG. 6.

In another embodiment of the invention, a scale (not shown) may be configured to output aggregate particle weight information to the computer 200. In one aspect of this embodiment, each measured aggregate particle is placed on the scale following measurement of the desired dimensions. Once the measured weight has stabilized or been dampened to within a threshold tolerance, such as but not limited to +/−1 gram, the scale may then automatically output to the computer the weight data for the aggregate particle. Following measurement of all of the aggregate particles, the computer 200 may then calculate, for example, the weighted average of the total sample or the actual ratio of each individual particle.

Although the preferred embodiment of the invention utilizes a digital caliper as the measurement device 100, owing to its combination of simplicity, low cost, and accuracy, the measurement device 100 could include any device capable of determining the required dimensions. Thus, the invention can also include, but is not limited to, laser measurement devices, laser imaging or scanning devices, or acoustic measurement devices such as conventionally known laser interferometers or laser ranging devices, active or passive imaging systems such as CCDs, lasers, or cameras. For example, an active system could include an amplitude-modulated ranger, which transmits a laser signal to a target object and uses the reflected laser signal from the target object to a detector, such as a silicon avalanche photodiode (APD), to determine distance to the object. The optical signal is filtered to pass only the transmitted optical frequency, and the electronic detector signal is filtered to pass only the amplitude modulated frequency. An electronic phase detector then measures the phase difference between the transmitted signal and the received signal, which is proportional to the target object distance. This distance could then be subtracted from a known or measured distance of a flat surface upon which the target object rests to determine a dimension of the target object at the measured point.

Alternatively, another type of active measurement device 100 could include one or more lasers employing "time-of-flight" measurement of short infrared or near-infrared pulses. In these systems, the actual time of flight from output of the pulse from the laser to receipt of the reflected pulse by the detector is measured and converted into a distance using the known speed of the pulse. This known distance may then be converted into a dimension of the target object at the measured point, as noted above.

Still further, alternate measurement devices 100 comprising any type of modulated output signal (e.g., a modulated radiation such as focused optical radiation (e.g., laser beam) or radio or sonic signals) may be employed so long the alternate imaging systems can provide, at a minimum, range information to a measured point of the target object. The target object will reflect the radiation and provide a reflected signal which can be detected at either the source of the original radiation or at an adjacent site. The detected radiation will exhibit a phase shift or other characteristic difference, such but not limited to a time-shift, relative to a reference signal derived from the source of the original radiation. In this aspect, the phase shift may be used to determine the distance to the target object in a manner known to those skilled in the art utilizing known information about the system, the output signal, and the received signal. Still further, scannerless imaging systems may be used. Examples of such scannerless imaging systems are described in U.S. Pat. No. 6,088,086 to Muguira et al. and to U.S. Pat. No. 4,935,616 to Scott. These references provide scannerless imaging systems that are capable of providing range information, which may be converted into target object dimensional information and used in accord with the invention.

Additionally, passive systems could be employed in accord with the invention to obtain the desired range data. For example, cameras or CCDs could be used. One aspect of this involves stereo sculpture, stereo display, or stereo vision wherein three dimensional objects are imaged and re-created from stereo information gathered by a stereo pair including, for example stereo cameras or lasers, in a manner known to those skilled in the art. Thus, topo maps can be created by machines using stereo pairs as input. Moreover, stereo vision image data may be accomplished using a single camera wherein various types of mechanical or electro-optic devices can block the light through parts of the optical path to create field sequential stereo pairs, as discussed, for example, in U.S. Pat. No. 5,028,994 to Miyakawa, et al. titled "Synchronized Three Dimensional Imaging Apparatus". Thus, the invention contemplates incorporation of any device able to provide target object dimensional information including but not limited to active systems (e.g., lasers outputting laser pulses and receiving a corresponding reflected pulse) and passive systems (e.g., charge coupled devices, CCDs, or camera based systems which passively receive external signals) in any combination. Thus, an entirely active measurement device 100 or system could be used, a combined active and passive measurement device or system 100 could be used, or an entirely passive measurement device or system 100 could be used. Any of these combinations could be achieved in accord with the invention and with techniques known to those skilled in the art.

Still further, the measurement device or system 100 may comprise a simple fixed single laser, which determines the distance to a single point on the object placed in the laser signal's flight path; a single laser configured to output a scanning beam along one or more axes, as noted above; a single laser utilizing conventional optics and a beam splitter to cause the output laser signal to approach the beam from a plurality of directions; or multiple lasers.

Although the computer 200 illustrated in FIGS. 1–5 is preferably a laptop or notebook computer, or other portable computing device such as a handheld computing device, the computer 200 need only be required to receiving digitized information through a suitable port or interface, process the data, and output data through an appropriate port or interface. As described in more detail below, the port or interface can comprise a hardwired interface or could rely on data transmitted to the device by a carrier wave or signal. The computer 200 is loaded with a suitable programs, such as a spreadsheet or database program or application, or instruction sets or macros capable of capturing the digitized measurement data supplied by the measurement device 100, and applying predetermined operations therewith. By way of example only, a suitable example of such software is Excel® marked by Microsoft. Additional discussion of the computer system in accord with the invention is provided below.

The switch 300, which may be foot operated, hand operated, voice operated, or configured to operate in another manner conducive to obtaining measurements in accord with the invention, is operatively connected with the digital caliper 100 or other measurement device, as well as the computer or computer interface device. In one aspect of the invention, operation of the switch 300 triggers the upload of measurement data from the digital caliper 100 or other measurement device. It is preferred to allow the operator to control output of measurement data to the computer 200 using such a switch to permit the operator to properly orient the aggregate particle, or reorient the aggregate particle, to obtain the proper measurements. The switch may be disposed in a variety of locations in accord with the invention and may assume a variety of forms other than the examples noted above. For example, the switch may be located on the handle/knob 108 in the form of a button or trigger. Alternatively, the switch could include a light beam or light curtain which, when the light beam(s) is broken such as by the movement of a limb, the switch is activated.

As noted above, the Multiple Ratio Analysis or MRA technique of the present invention provides not only an apparatus for measuring the dimensions of a target object, such as an aggregate particle, but also provides a method of categorizing the various particle shapes found in an aggregate sample. Improved definition of the particle shapes found within a coarse sample of aggregate particles leads to improved mix design procedures for performance optimizing combined gradations based around particle shapes.

Thus, the MRA technique of the invention utilizes the aforementioned measuring device or system 100, such as the digital caliper, to quickly and accurately determines the various coarse aggregate particle shapes found in an aggregate sample and provide an accurate picture of an aggregate sample's particle shapes by evaluating the sample on a plurality of different ratios, such as but not limited to five or more (i.e., <2:1, 2:1 to 3:1, 3:1 to 4:1, 4:1 to 5:1, >5:1), as shown in FIG. 6, whereas conventional techniques only evaluate one ratio. The computer 200 and associated software, such as a spreadsheet, use the measurement data to calculate the ratios of interest in accord with the invention and output to the operator and/or another device connected to the computer one or more signals indicative of the calculated ratio or ratios as shown, for example, in FIG. 10.

To help prevent operator error, the displayed ratios may be color-coded or otherwise differentiated on the spreadsheet display(s). In one embodiment, each of the selected plurality of ratios is assigned an arbitrary color or distinctive symbol or shape, or any combination thereof. These colors and/or shapes may preferably correspond to colors of bins used to receive particles of the respective ratio and/or symbols/shapes used to designate bins receiving particles of the respective ratio. For example, yellow could be assigned to particles having a ratio of <2:1, blue for 2:1 to 3:1, green for 3:1 to 4:1, purple for 4:1 to 5:1, and red for >5:1. Thus, upon entry of the first and second measurements into the computer 200, the computer would output a signal to a display device, in the form of a color, to tell the technician to place a 1:1 particle in the yellow bin. This relieves the technician of the burden of reading numbers off of the computer 200 display. Likewise, the output signal could comprise an audio message instructing the technician that the particle just measured is a "yellow" particle.

Figures 8, 9:
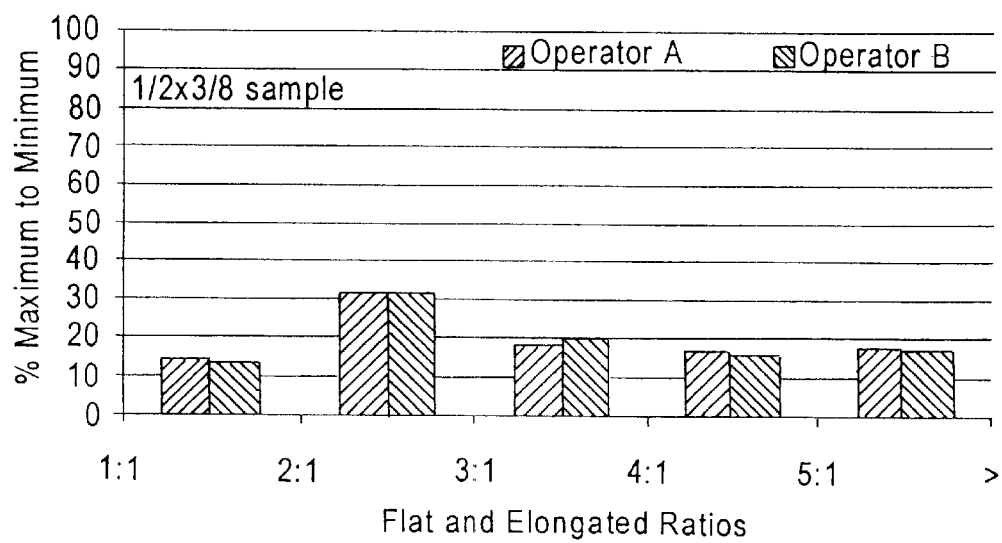
FIG. 8 is a depiction of a spreadsheet image showing the manner in which color can be used in conjunction with the data which is collected to code the MRA ratios which are developed by the software.
FIG. 9 is a bar graph which highlights the small amount of variation which is provided with the embodiment of the invention when used by an experienced operator and one who has no prior exposure to the arrangement.

The results of measurements taken on a sample of aggregate particles by two different operators with this device are shown in FIG. 9. One of the operators had never before measured particle shapes or performed any kind of aggregate testing. Thus, the measurement device 100 and method of the invention may be easily utilized, even by unskilled persons.

Figure 11:
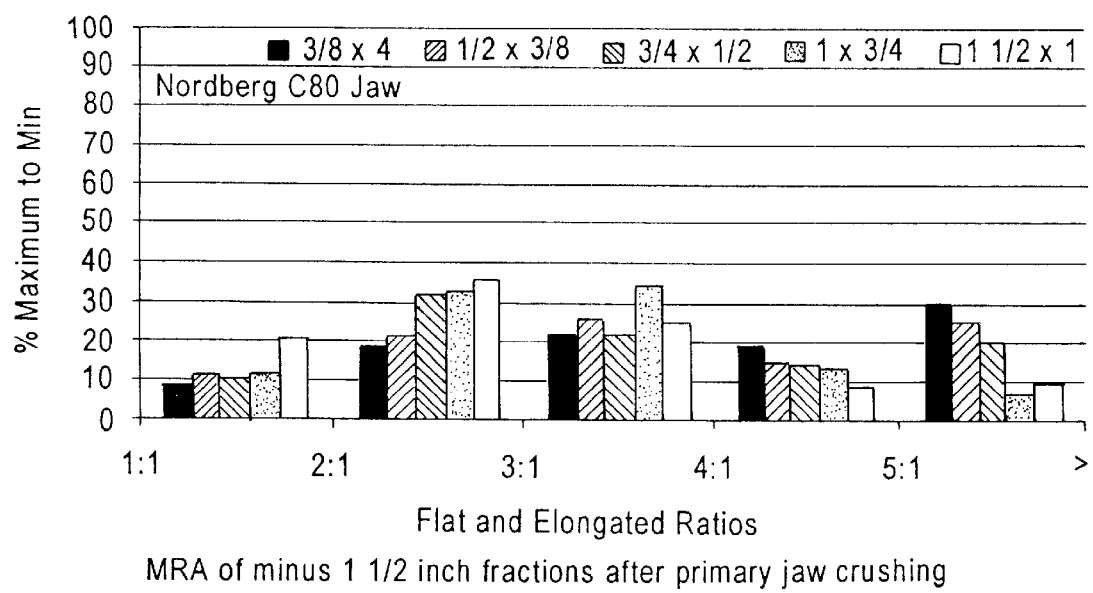
FIG. 11 depicts the MRA of 1.5 inch fractions after primary jaw crushing.
Figure 12:
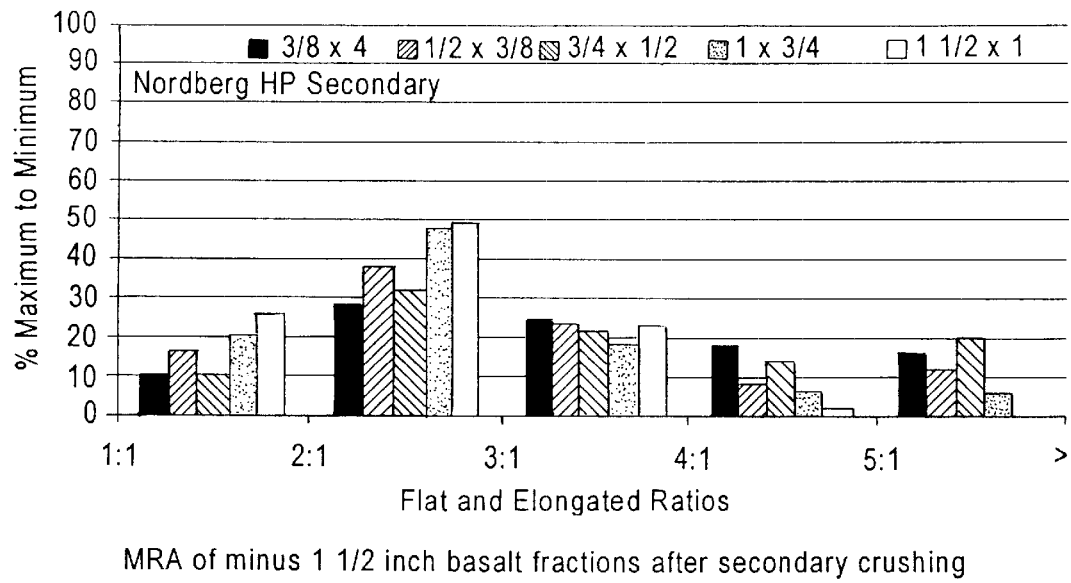
FIG. 12 depicts the MRA of 1.5 inch basalt fractions after secondary crushing.
Figure 13:
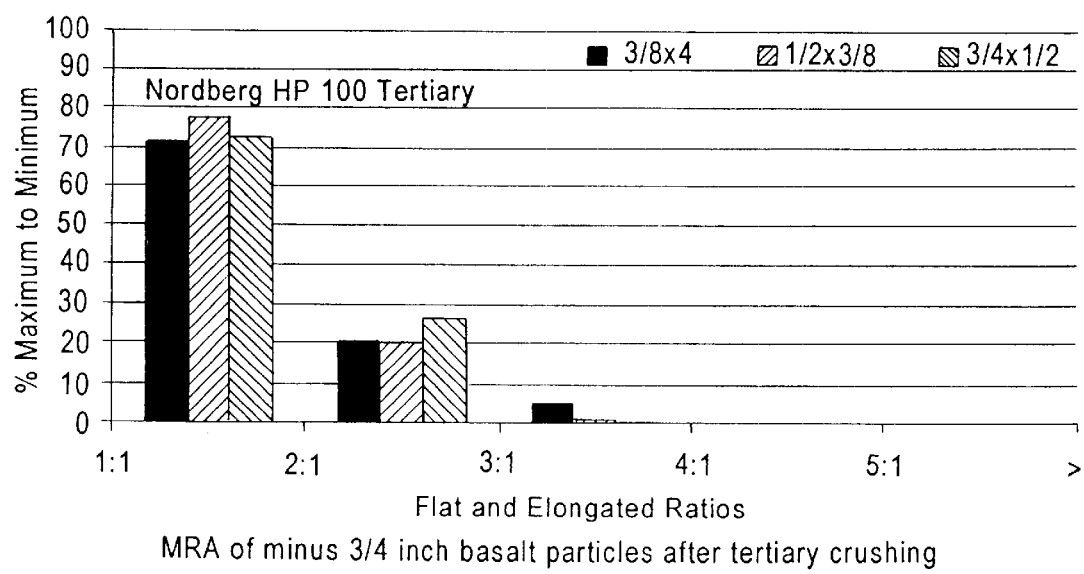
FIG. 13 depicts the MRA of minus ¾ inch basalt particles after tertiary crushing.

Thus, as shown in FIGS. 11–13, for example, the MRA technique can help identify particle shape issues in the production process by providing a complete picture of the particle shapes at each stage of production. FIGS. 11–13 show particles retained on the 1 inch sieve through the #4 sieve at each stage of a production process. The material measured is a hard basalt that is difficult to crush. Extremely hard materials like this tend to "shatter" rather than crush and therefore produce many flat and elongated particles. As can be seen from this example, application of the correct crushing technology to fit the situation can turn flat and elongated particles into cubical particles. Also, particles from the primary and secondary crushers in the following examples are to be benefited by passing through the tertiary crusher before reaching finished product stockpiles. The samples are used to illustrate how well MRA can identify changes occurring at each stage of crushing.

Figure 14:
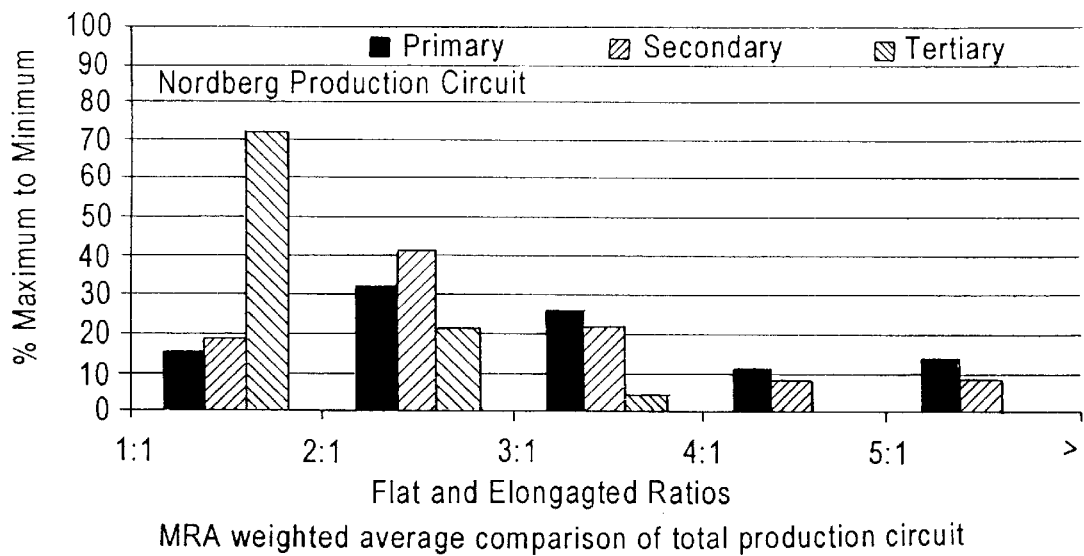
FIG. 14 depicts the MRA weighted average comparison of total production circuit.

FIG. 11 shows particles retained on the 1 inch and smaller sieves from a 6-inch minus (primary) jaw crusher product. FIG. 12 shows the same particle sizes after passing through a secondary high-speed cone crusher. FIG. 13 shows the same particles after the particles pass through another high-speed cone crusher (tertiary). Only particles smaller than ¾" were allowed to reach finished product stockpiles after this crushing stage. Particles larger than ¾" are returned to the crushing circuit. FIG. 14 compares the weighted average of all three stages of crushing.

Thus, MRA analysis of finished products in accord with the invention can be used as a tool for evaluating product consistency in various stages of the production process. Additionally, trending data of aggregate particle size may be used, over time, to monitor the effectiveness of the crushers and crusher wear liners in the production circuit.

Figure 15:
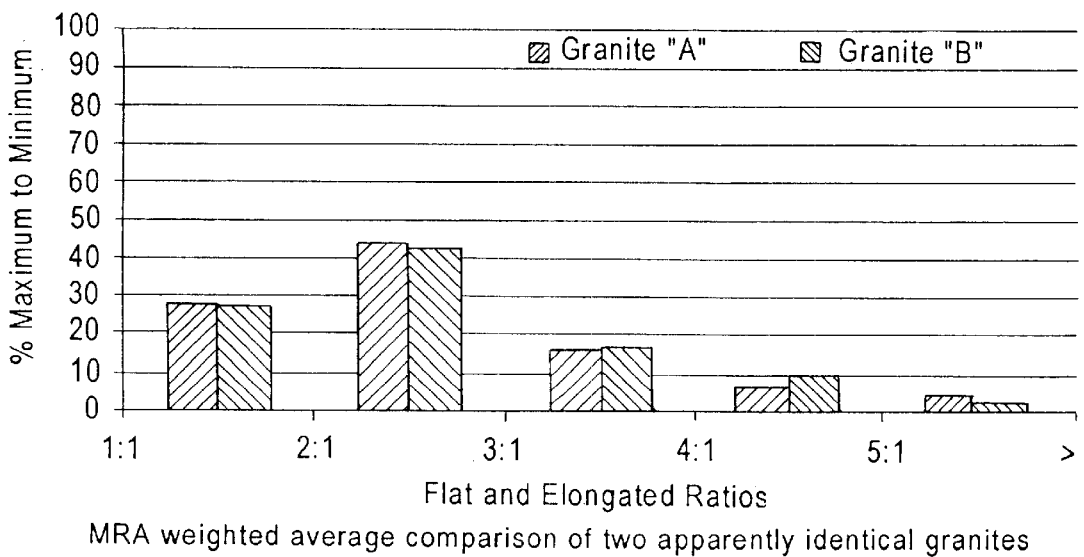
FIG. 15 depicts the MRA weighted average comparison of two apparently identical granites.
Figure 16:
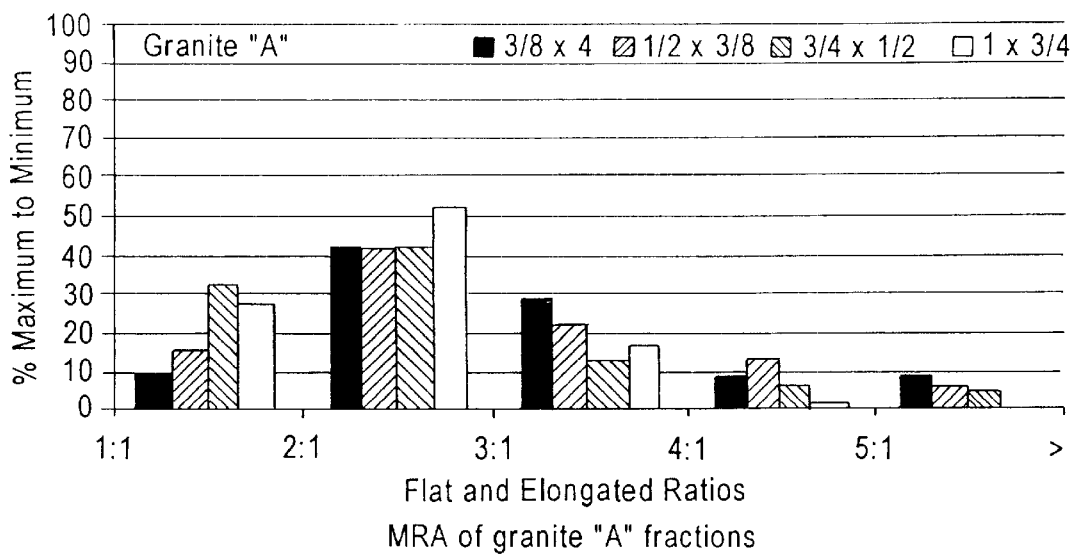
FIGS. 16 and 17 are MRA of a first and second different groups of granite fractions.
Figure 17:
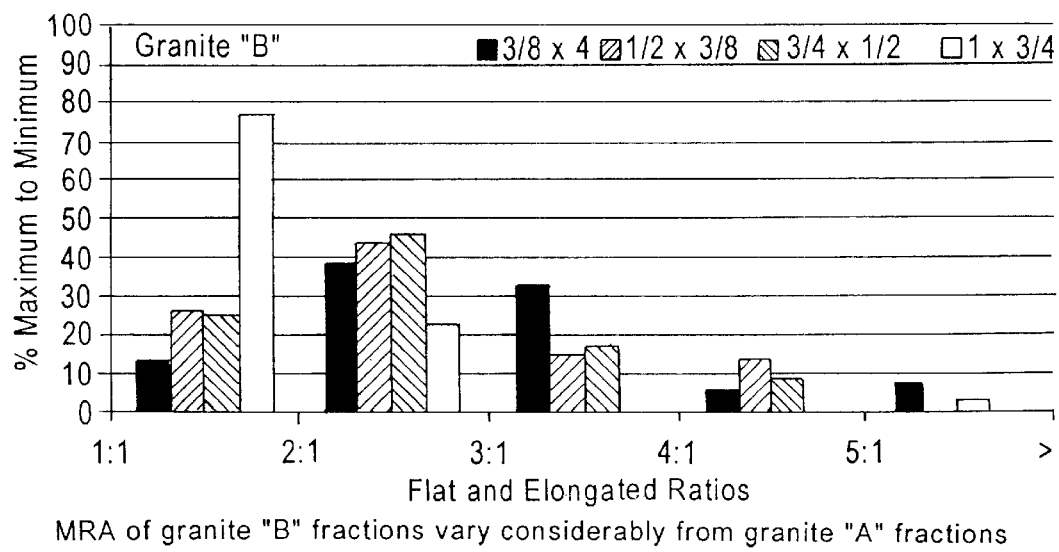

Conventional mix design procedures provide requirements on flat and elongated particles but do not provide enough information about particle shapes to permit modification or optimization of the mix design in accord with the variable of particle shape. For example, the shape may even be used to differentiate between materials. FIG. 15 compares two virtually identical granites based only on their weighted averages. However, when the aggregate particle shape or fractional ratios of the aggregate particles are taken into account, as shown in FIGS. 16 and 17, many differences can be seen. This information can then be used by a mix designer to optimize the combined gradation that best fits the particle shapes found in the aggregates and can be used by a process engineer to optimize the tooling, tooling settings, or process flow to obtained desired results. For example, highly angular aggregates should be blended so that the combined gradation is near the maximum density line, and passes through a predetermined restricted zone. Otherwise the voids in the mineral aggregate (VMA) is too high and flushing problems will occur. Highly cubical aggregates should be combined away from the maximum density line in order to achieve enough VMA. There is an optimum combined gradation for each of the particle shapes. Using the identical combined gradation for cubical and angular particle shapes will produce mixes with very different properties.

MRA can also be used to identify when certain combined gradations should be used. Rather than force aggregate producers to achieve uniform particle shapes across all geologic types, MRA analysis can be used to identify the particle shapes and therefore the appropriate combined gradation suitable for each material. This will allow aggregate producers to utilize the correct crushing technology to fit the geologic type of material in the deposit and therefore help contain increasing production costs. There is an optimum gradation for each combination of particle shapes, allowing each type of particle shape to be successfully used.

Figure 18:
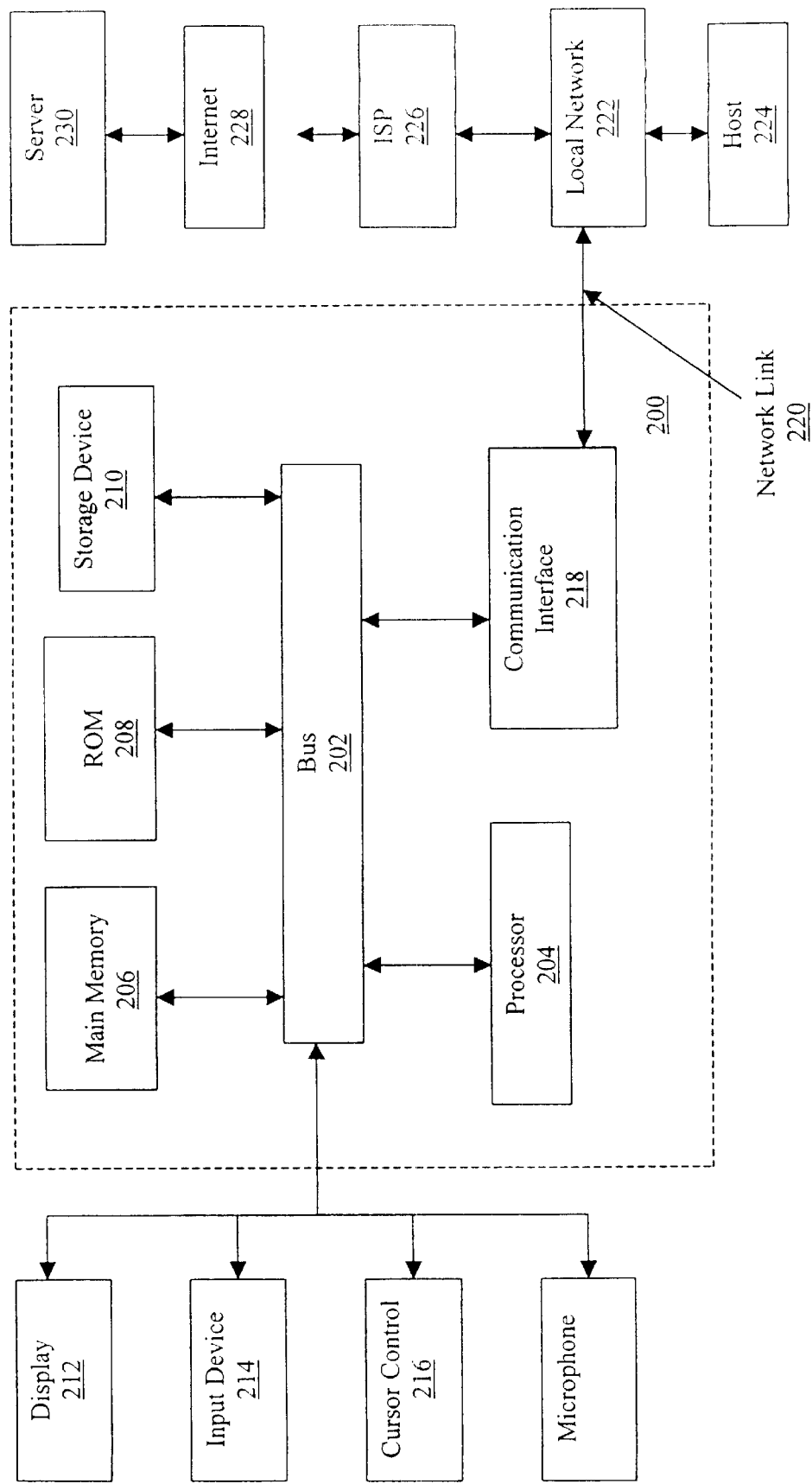
FIG. 18 illustrates a computer system utilizable in accord with the invention.

FIG. 18 depicts a computer 200 system in accord with the invention. Supporting equipment typically comprises a video color display monitor 210, a printer 220, a central processing unit (CPU) 230, interfacing electronics 240, and a keyboard or other data entry means 260. CPU 230 includes a bus 232 or other communication mechanism for communicating information, and one or more processors such but not limited to Intel Pentium III/IV processors coupled with bus 232 for processing information. CPU 230 also includes a main memory 236, such as a random access memory (RAM) or other dynamic storage device, coupled to bus 232 for storing information and instructions to be executed by the processor(s). Main memory 236 also may be used for storing temporary variables or other intermediate information during execution of instructions to be executed by the processor(s). CPU 230 further includes a read only memory (ROM) 238 or other static storage device coupled to bus 232 for storing static information and instructions for the processor(s). A storage device 270, such as a magnetic disk or optical disk, is provided and coupled to bus 232 for storing and providing information and instructions.

CPU 230 may be coupled via bus 232 to monitor 210, such as a cathode ray tube (CRT), for displaying information to a computer user. Input device or data entry means 260, including alphanumeric and other keys or a microphone to enable voice activated functions, is coupled to bus 232 for communicating information and command selections to the processor(s). Other types of user input devices may include cursor control, such as a mouse, a trackball, the aforementioned foot operated switch 300, or cursor direction keys for communicating direction information and command selections to the processor(s) and for controlling cursor movement on display 210.

Transmission media for data to and from processor(s) and associated devices, including bus 232 may comprise coaxial cables, metal wire or metal layers and fiber optics. Transmission media can also take the form of acoustic or light waves, such as those generated during radio frequency (RF) and infrared (IR) data communications. CPU 230 also may include a communication interface 280 coupled to bus 232 to provide two-way data communication coupling to a link, such as a network link 282, by sending and receiving electrical, electromagnetic or optical signals that carry digital data streams representing various types of information. It will be appreciated that various forms of output devices may be operatively connected to the CPU 230 through the transmission media to be controlled thereby.

The computer 230 is used to process the data obtained by the measurement system 100 output the data in a meaningful form. In accord therewith, this function is provided by computer 230 in response execution by the processor of one or more sequences of instructions contained in main memory 236. Such instructions may be read into main memory 236 from a computer-readable medium, such as storage device 270. Execution of the sequences of instructions contained in main memory 236 causes the processor to perform the process steps described herein. In alternative embodiments, hard-wired circuitry may be used in place of or in combination with software instructions and it is to be understood that no specific combination of hardware circuitry and software are required.

The instructions may be provided in any number of forms such as source code, assembly code, object code, machine language, compressed or encrypted versions of the foregoing, and any and all equivalents thereof. "Computer-readable medium" refers to any medium that participates in providing instructions to the computer 230 for execution and "program product" refers to such a computer-readable medium bearing a computer-executable program. The computer usable medium may be referred to as "bearing" the instructions, which encompass all ways in which instructions are associated with a computer usable medium.

Computer-readable mediums include, but are not limited to, non-volatile media, volatile media, and transmission media. Non-volatile media include, for example, optical or magnetic disks, such as storage device 270. Volatile media include dynamic memory, such as main memory 236. Transmission media include coaxial cables, copper wire and fiber optics, including the wires that comprise bus 232. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to computer 230 for execution. For example, the instructions may initially be borne on a magnetic disk of a remote computer. The remote computer can load the instructions into its dynamic memory and send the instructions over a telephone line using a modem. A modem local to computer 230 can receive the data on the telephone line and use an infrared transmitter to convert the data to an infrared signal. An infrared detector coupled to bus 232 can receive the data carried in the infrared signal and place the data on bus 232. Bus 232 carries the data to main memory 236, from which computer 230 retrieves and executes the instructions.

Computer system 200 also may include a communication interface 218 coupled to bus 202. For example, communication interface 218 may be an integrated services digital network (ISDN) card or a modem to provide a data communication connection to a corresponding type of telephone line. As another example, communication interface 218 may be a local area network (LAN) card to provide a data communication connection to a compatible LAN. Wireless links may also be implemented. In any such implementation, communication interface 218 sends and receives electrical, electromagnetic or optical signals that carry digital data streams representing various types of information.

Network link 220 typically provides data communication through one or more networks to other data devices. For example, network link 220 may provide a connection through local network 222 to a host computer 224 or to data equipment operated by an Internet Service Provider (ISP) 226. ISP 226 in turn provides data communication services through a worldwide packet data communication network 228, such as the "Internet." Local network 222 and Internet 228 both use electrical, electromagnetic or optical signals that carry digital data streams. The signals through the various networks and the signals on network link 220 and through communication interface 218, which carry the digital data to and from computer system 200, are exemplary forms of carrier waves transporting the information.

The instructions received by main memory 236 may optionally be stored on storage device 270 either before or after execution by computer 230. The CPU 230 advantageously accesses memory media including floppy disks, tape drives, and hard disk drives, as previously indicated, may also output control signals to the measurement device or system 100, particularly if the measurement device includes a laser measurement device. Interface electronics 240 convey and format signals from the measurement system components to the computer 230 and commands from computer 230 to the system components. Interface electronics 240 employs conventional circuitry, such as standard printed circuit cards, and utilize standard data transmission formats.

Multiple Ratio Analysis is a new concept in describing aggregate particle shapes by identifying the amount of particles found in five different ratios rather than one ratio. In addition, a new low-cost measuring device is provided that accurately and easily determines multiple ratios found within a sample. This allows mixes to be designed by first determining the various particle shapes involved, and then using the correct combined gradation to fit the particle shapes for optimum performance. This common sense approach can be used to address the many different geologic types used for construction aggregates, and help designers with reducing risks and improving performance.

Only several embodiment of the invention are shown to illustrate its versatility as shown and described in the present disclosure. It is to be understood that the invention is capable of use in various other combinations and environments and is capable of changes or modifications within the scope of the inventive concept as expressed herein. Moreover, although illustrative examples of the method of the present invention were discussed, the present invention is not limited by the examples provided herein and additional variations of the invention are embraced by the claims appended hereto.

What is claimed is:

1. A method of multiple ratio analysis comprising the steps of:
   measuring a first maximum dimension of a particle;
   measuring a second maximum dimension of a particle in a direction substantially perpendicular to said first maximum dimension;
   inputting said first maximum dimension and said second maximum dimension into a computer having a processor;
   computing, using said computer, a particle ratio of said first maximum dimension to said second maximum dimension for the measured particle; and
   classifying said particle ratio into one of a predetermined plurality of different ratio ranges, each of said plurality of different ratios representative of a different range of particle shapes.

2. A method of multiple ratio analysis in accord with claim 1, wherein said first maximum dimension comprises a substantially maximum dimension of particle length.

3. A method of multiple ratio analysis in accord with claim 2, wherein said second maximum dimension comprises a substantially maximum dimension of a lesser one of particle width and thickness.

4. A method of multiple ratio analysis in accord with claim 3, wherein said predetermined plurality of different ratio ranges consists of ratio ranges of less than 2:1, 2:1 to 3:1, 3:1 to 4:1, 4:1 to 5:1, and greater than 5:1.

5. A method of multiple ratio analysis in accord with claim 4, further comprising:
   weighing the particle; and
   inputting the weight of the particle into said computer.

6. A method of multiple ratio analysis in accord with claim 4, further comprising:
   measuring a first maximum dimension for a plurality of particles;
   measuring a second maximum dimension for a plurality of particles in a direction substantially perpendicular to said first maximum dimension;
   inputting said first maximum dimension and said second maximum dimension of said plurality of particles into a computer having a processor;
   computing, using said computer, a particle ratio of said first maximum dimension to said second maximum dimension for each of the measured plurality of particles; and
   classifying each of said particle ratio into one of a predetermined plurality of different ratio ranges, each of said plurality of different ratios representative of a different range of particle shapes.

7. A method of multiple ratio analysis in accord with claim 6, further comprising:
   weighing said plurality of particles; and
   inputting the weight of each of said plurality of particles into said computer.

8. A method of multiple ratio analysis in accord with claim 7, further comprising:
   computing a MRA distribution for said plurality of different ratio ranges for a sieve;
   determining, using said computer, if said MRA distribution comports to an acceptable range of particle shapes in accord with said sieve.

9. A method of multiple ratio analysis in accord with claim 8, further comprising:
   computing a plurality of MRA distributions for said plurality of different ratio ranges for a plurality of sieves;
   determining, using said computer, if said MRA distributions comport to acceptable ranges of particle shapes in accord with respective ones of said plurality of sieves.

10. A method of multiple ratio analysis in accord with claim 9, further comprising:
    outputting a control signal from the computer to control at least one process parameter to adjust at least one process parameter and to control an output of one or more of said plurality of sieves in accord with said MRA distributions and a predetermined process mix specification.

11. An apparatus for multiple ratio analysis comprising:
    a measurement device configured to measure a dimension of an aggregate particle along at least one axis at a time;
    a computer;
    a computer-readable medium bearing an instruction set executable by the computer to perform the steps of:
      calculating an aggregate particle ratio for the aggregate particle by determining a ratio of a first maximum dimension and a second maximum dimension of the aggregate particle; and
      classifying said aggregate particle ratio into one of a predetermined plurality of different aggregate particle ratio ranges, each of said plurality of different aggregate particle ratios representative of a different range of aggregate particle shapes.

12. An apparatus as set forth in claim 11, wherein said measurement device is configured to output signals corresponding to said first maximum dimension and said second maximum dimension to the computer, and wherein said computer is configured to receive said output signals.

13. An apparatus as set forth in claim 12, wherein said measurement device comprises a digital caliper.

14. An apparatus as set forth in claim 12, wherein said measurement device comprises at least one of a laser, a camera, a CCD, and an acoustic measuring device.

15. An apparatus as set forth in claim 13, wherein said first maximum dimension of an aggregate particle comprises a substantially maximum dimension of particle length.

16. An apparatus as set forth in claim 15, wherein said second maximum dimension of an aggregate particle comprises a substantially maximum dimension of a lesser one of particle width and thickness.

17. An apparatus as set forth in claim 16, wherein said predetermined plurality of different aggregate particle ratio ranges consists of ratio ranges of less than 2:1, 2:1 to 3:1, 3:1 to 4:1, 4:1 to 5:1, and greater than 5:1.

18. An apparatus as set forth in claim 17, further comprising a scale for measuring a weight of said aggregate particle.

19. An apparatus as set forth in claim 18, wherein said scale is a digital scale configured to output a weight of said aggregate particle to said computer.

20. A method of multiple ratio analysis in accord with claim 18, wherein said scale is configured to measure a weight of a plurality of aggregate particles.

21. An apparatus as set forth in claim 20, wherein said instruction set comprises instructions for performing the steps of:

computing a MRA distribution for a plurality of aggregate particles for said plurality of different aggregate particle ratio ranges for a sieve;

determining, using said computer, if said MRA distribution comports to an acceptable range of aggregate particle shapes in accord with said sieve.

22. An apparatus as set forth in claim 21, wherein said instruction set comprises instructions for performing the steps of:

computing a plurality of MRA distributions for a plurality of aggregate particles for said plurality of different aggregate particle ratio ranges for a plurality of sieves;

determining, using said computer, if said MRA distributions comport to acceptable ranges of aggregate particle shapes in accord with respective ones of said plurality of sieves.

23. An apparatus as set forth in claim 22, wherein said instruction set comprises instructions for performing the steps of:

outputting a control signal from the computer to control at least one process parameter to adjust at least one process parameter and to control an output of one or more of said plurality of sieves in accord with said MRA distributions and a predetermined aggregate particle process mix specification.

* * * * *